(12) United States Patent
Katsumoto et al.

(10) Patent No.: US 10,151,740 B2
(45) Date of Patent: Dec. 11, 2018

(54) CONTACT STRUCTURE BODY ELECTRICAL MEASURING DEVICE FOR BIOLOGICAL SAMPLES

(71) Applicant: Sony Corporation, Tokyo (JP)

(72) Inventors: Yoichi Katsumoto, Tokyo (JP); Kazumasa Sato, Tokyo (JP); Daisuke Terakado, Saitama (JP)

(73) Assignee: Sony Corporation, Tokyo (JP)

( * ) Notice: Subject to any disclaimer, the term of this patent is extended or adjusted under 35 U.S.C. 154(b) by 20 days.

(21) Appl. No.: 15/326,966

(22) PCT Filed: Jul. 13, 2015

(86) PCT No.: PCT/JP2015/003533
§ 371 (c)(1),
(2) Date: Jan. 17, 2017

(87) PCT Pub. No.: WO2016/013176
PCT Pub. Date: Jan. 28, 2016

(65) Prior Publication Data
US 2017/0212097 A1  Jul. 27, 2017

(30) Foreign Application Priority Data

Jul. 24, 2014 (JP) ................................ 2014-150634
May 22, 2015 (JP) ................................ 2015-104818

(51) Int. Cl.
*G01N 33/487* (2006.01)
*G01N 27/22* (2006.01)
(Continued)

(52) U.S. Cl.
CPC ..... *G01N 33/48707* (2013.01); *G01N 27/221* (2013.01); *G01N 27/226* (2013.01);
(Continued)

(58) Field of Classification Search
CPC ............... G01N 27/221; G01N 27/226; G01N 33/48707; G01N 33/49
(Continued)

(56) References Cited

U.S. PATENT DOCUMENTS 5,543,722 A * 8/1996 Suzuki ................. G01N 27/226
324/663
2004/0189311 A1 * 9/2004 Glezer ................... B01L 3/5027
324/444
(Continued)

FOREIGN PATENT DOCUMENTS

JP   2004-150879 A   5/2004
JP   2009-042141 A   2/2009
(Continued)

*Primary Examiner* — Jay Patidar
(74) *Attorney, Agent, or Firm* — Wolf, Greenfield & Sacks, P.C.

(57) ABSTRACT

A contact structure body for use in a measuring device. The contact structure includes a separator that physically separates a sample holder from a measuring circuit, and a contact probe configured to electrically connect an electrode of the sample holder to the measuring circuit, the contact probe comprising. The contact structure body may be part of a system for determining a characteristic of a sample. The system includes a sample holder for holding sample. The sample holder includes an electrode. The system also includes a measuring circuit for measuring at least one property of the sample.

21 Claims, 9 Drawing Sheets

(51) Int. Cl.
*G01N 33/49* (2006.01)
*G01N 27/02* (2006.01)

(52) U.S. Cl.
CPC ......... *G01N 33/49* (2013.01); *G01N 33/4905* (2013.01); *G01N 27/026* (2013.01)

(58) Field of Classification Search
USPC .......................................................... 324/663
See application file for complete search history.

(56) References Cited

U.S. PATENT DOCUMENTS

| | | |
|---|---|---|
| 2014/0162348 A1 | 6/2014 | Katsumoto et al. |
| 2015/0323480 A1* | 11/2015 | Brun ...................... G01N 33/49 422/73 |
| 2016/0327504 A1* | 11/2016 | Katsumoto ...... G01N 33/48757 |

FOREIGN PATENT DOCUMENTS

| | | |
|---|---|---|
| JP | 2010-181400 A | 8/2010 |
| JP | 2014-115256 A | 6/2014 |

\* cited by examiner

[Fig. 1A]
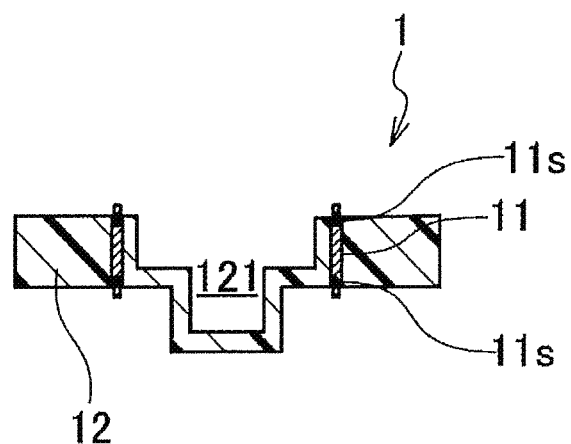

[Fig. 1B]
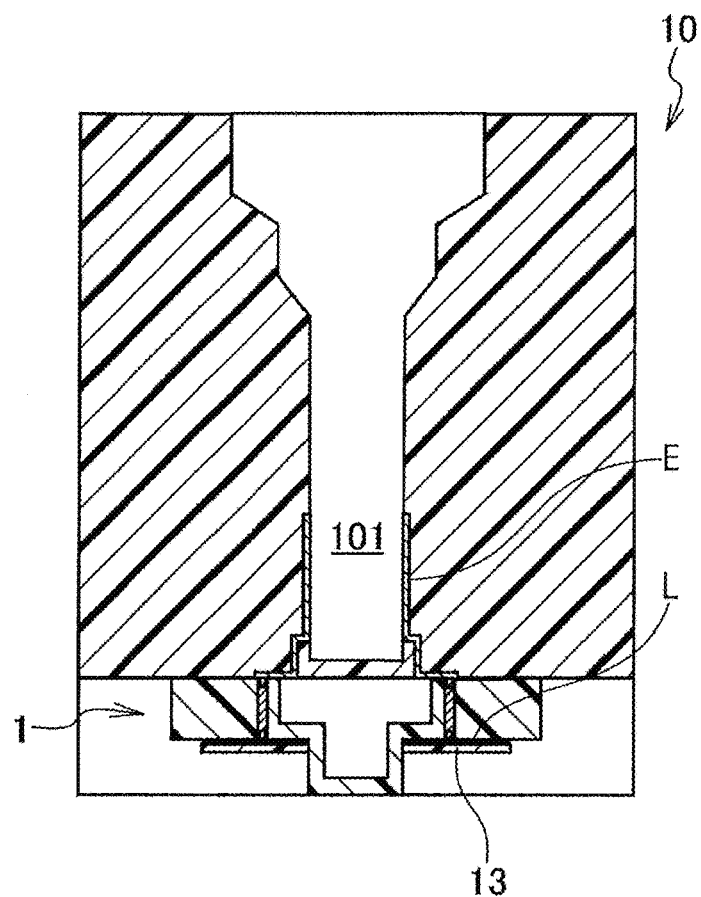
[Fig. 2A]
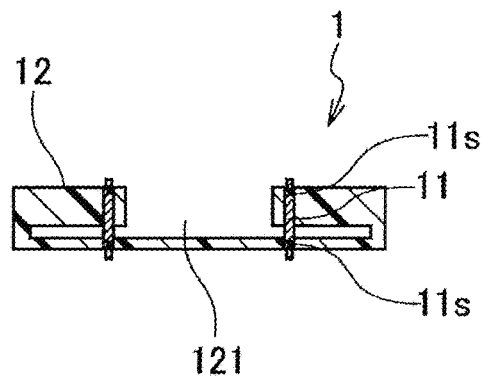

[Fig. 2B]
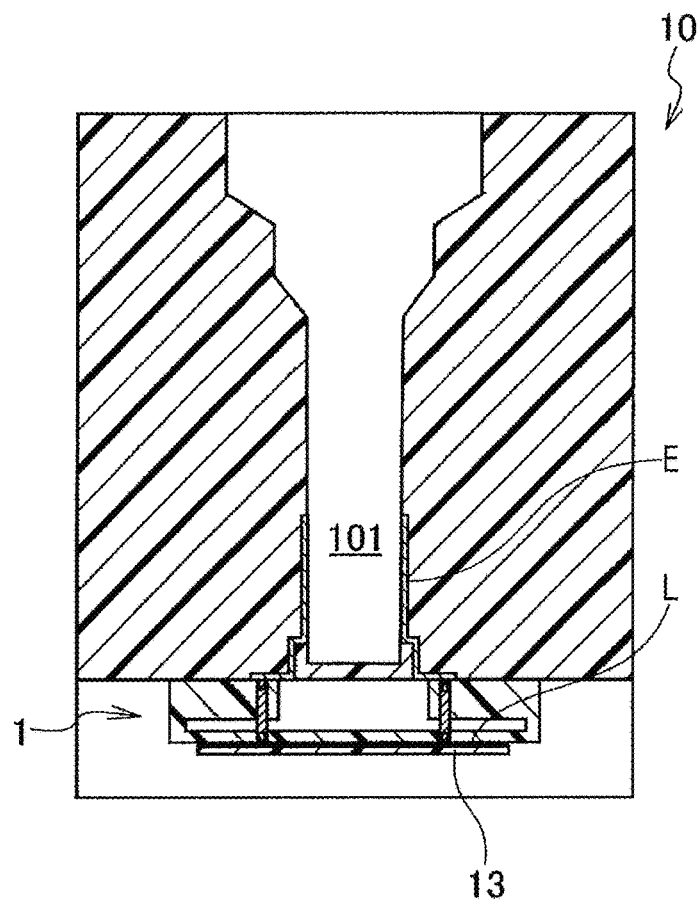
[Fig. 3A]
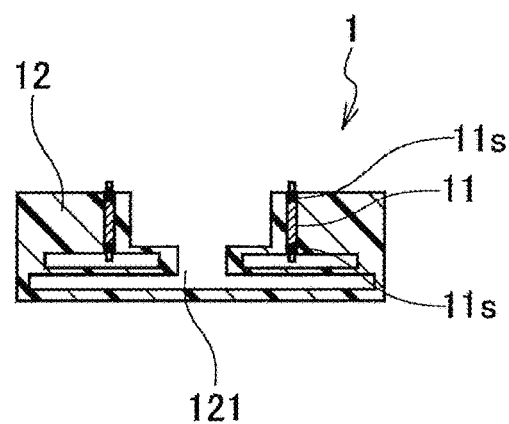

[Fig. 3B]
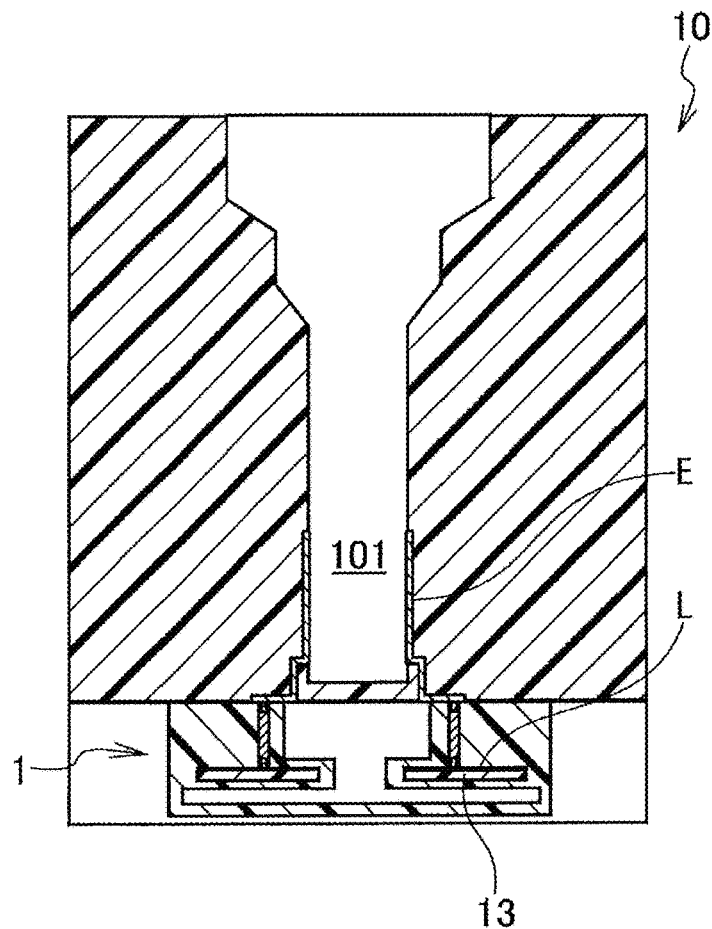
[Fig. 4A]
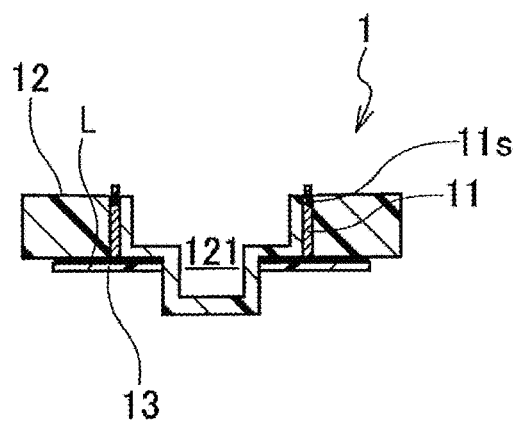

[Fig. 4B]
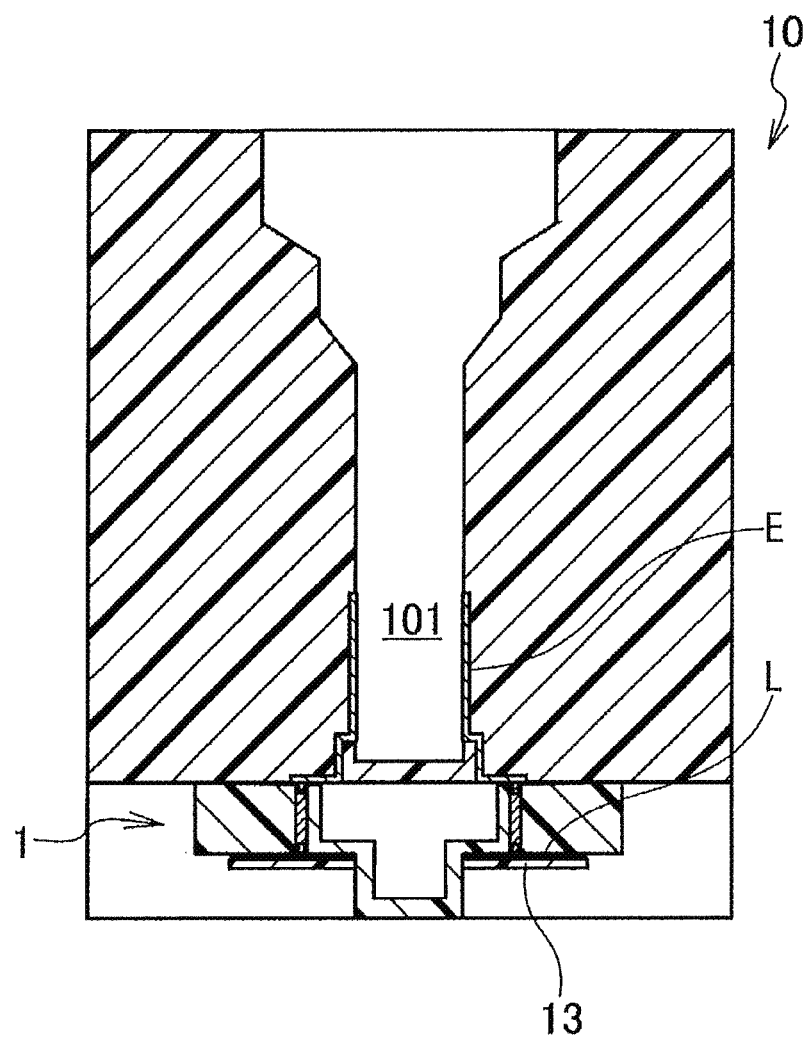

[Fig. 5]
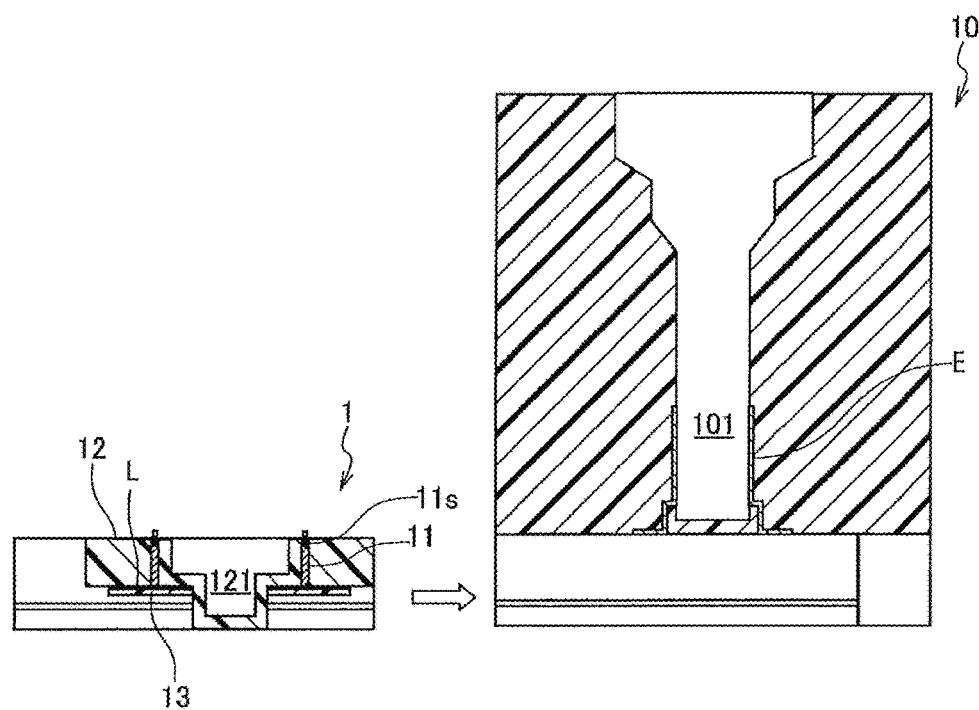

[Fig. 6]
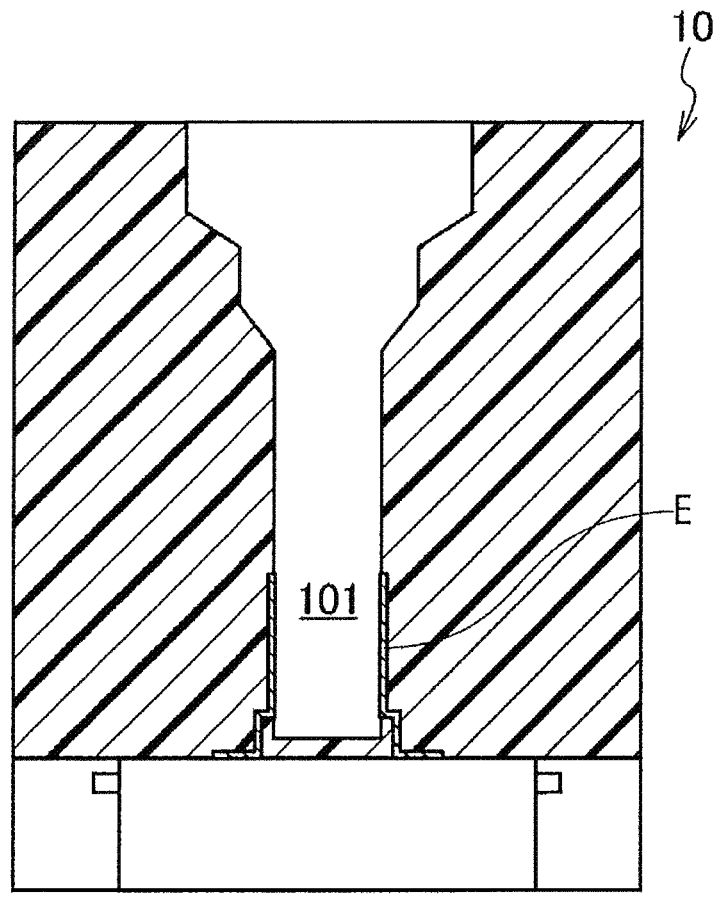
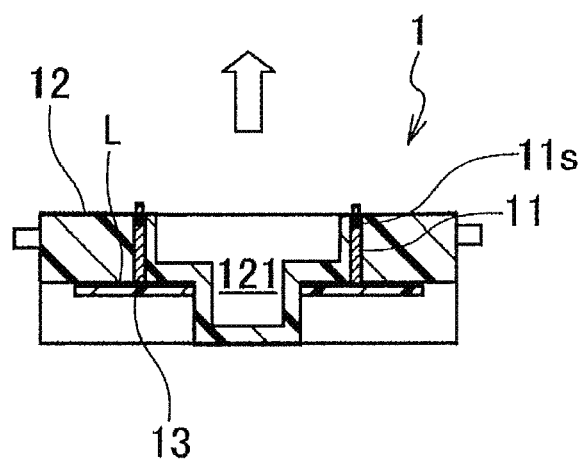

[Fig. 7]
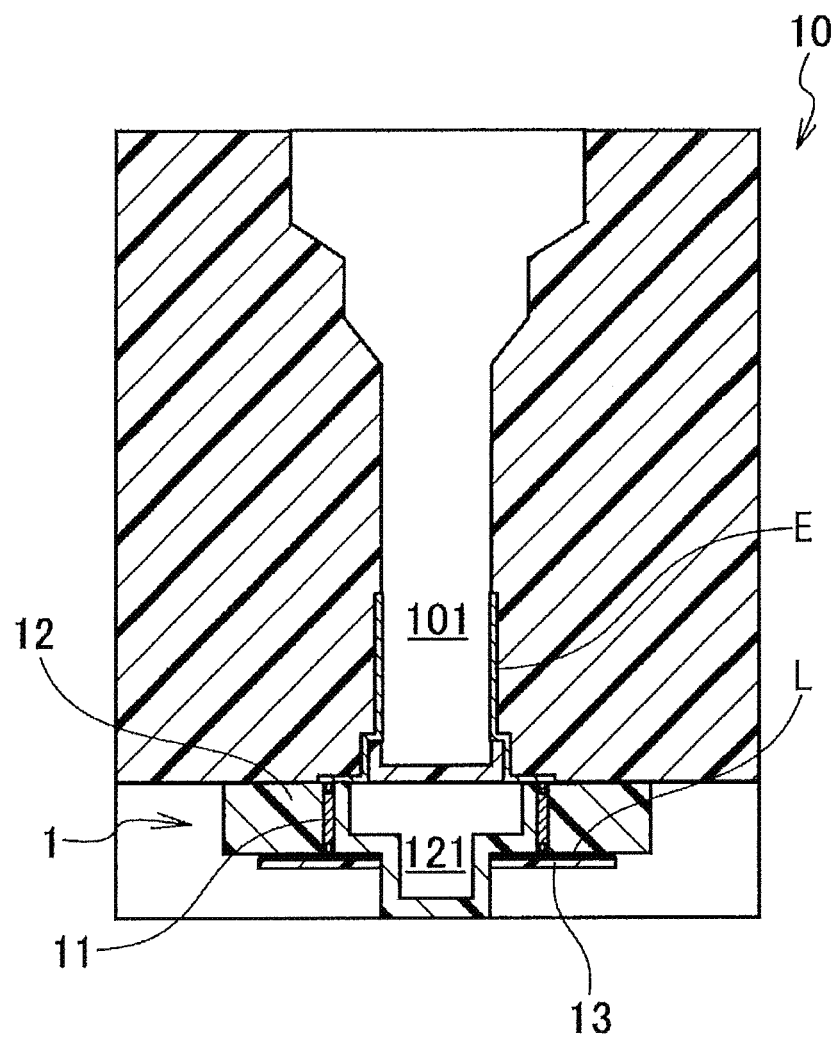

[Fig. 8]
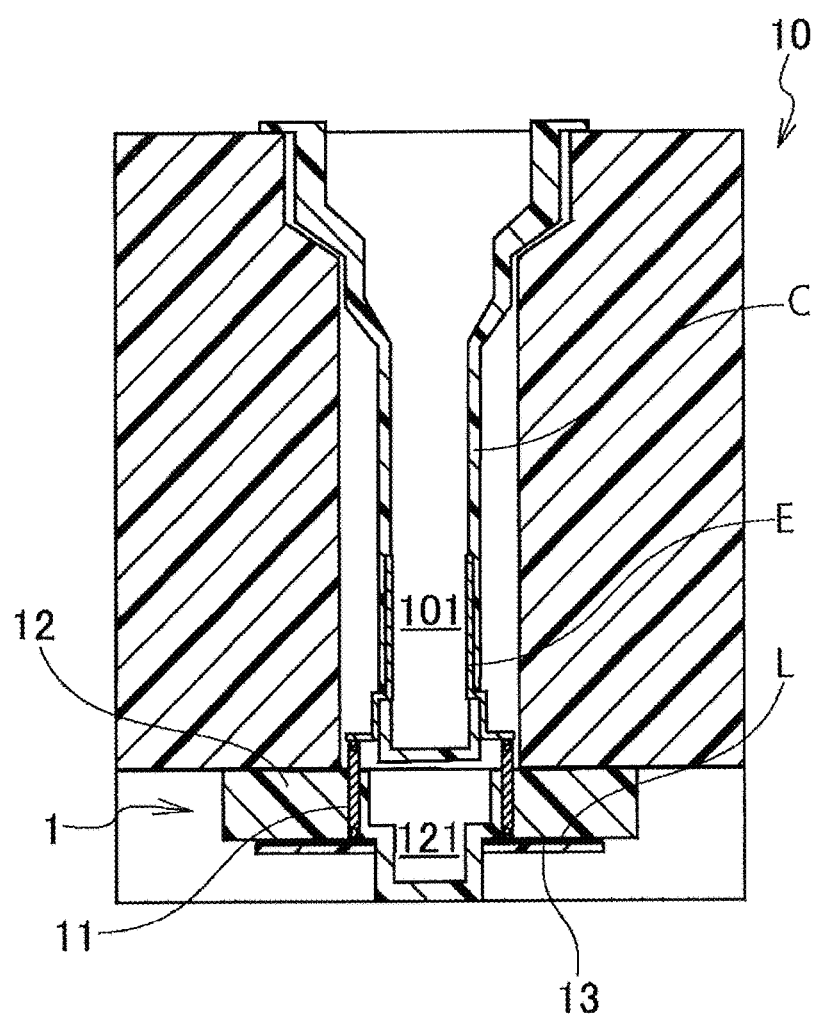

CONTACT STRUCTURE BODY ELECTRICAL MEASURING DEVICE FOR BIOLOGICAL SAMPLES

CROSS REFERENCE TO RELATED APPLICATIONS

This Application is a national stage filing under 35 U.S.C. 371 of International Patent Application Serial No. PCT/JP2015/003533, filed Jul. 13, 2015, titled "CONTACT STRUCTURE BODY AND ELECTRICAL MEASURING DEVICE FOR BIOLOGICAL SAMPLES USING CONTACT STRUCTURE BODY". Foreign priority benefits are claimed under 35 U.S.C. § 119(a)-(d) or 35 U.S.C. § 365(b) of Japanese application number 2015-104818, filed May 22, 2015 and Japanese application number 2014-150634, filed Jul. 24, 2014. The entire contents of these applications are incorporated herein by reference in their entirety.

TECHNICAL FIELD

The present technology relates to a contact structure body used for a device that electrically measures a biological sample. More specifically, the present technology relates to a structure body used for the contact between an electrode and a measuring circuit in a device that electrically measures a biological sample and to an electrical measuring device for biological samples using the contact structure body.

BACKGROUND ART

There are cases where the electrical characteristics of a biological sample are measured and the measurement results are used to determine the properties of the biological sample or to discriminate the types of cells etc. contained in the biological sample (e.g. see PTL 1). As the electrical characteristics to be measured, complex dielectric constant and its frequency dispersion (dielectric spectrum) are given. The complex dielectric constant and its frequency dispersion are generally calculated by using a solution holder or the like including electrodes for applying a voltage to a solution and measuring the complex capacitance or the complex impedance between the electrodes.

Furthermore, for example, PTL 2 discloses a technology in which information on blood coagulation is acquired from the dielectric constant of blood, and describes "a blood coagulation system analyzing device including a pair of electrodes, applying means for applying an AC voltage to the pair of electrodes at prescribed time intervals, measuring means for measuring the dielectric constant of blood disposed between the pair of electrodes, and analyzing means for analyzing the degree of working of a blood coagulation system using the dielectric constant of blood measured at the time intervals after the anticoagulant effect working on the blood is removed."

As a container for storing a biological sample when measuring the electrical characteristics of the biological sample, for example, PTL 3 discloses a container for the electrical measurement of biological samples in liquid forms, the container including at least a biological sample holding unit made of a resin for storing a biological sample in a liquid form and an electrically conductive unit fixed to the biological sample holding unit, in which the biological sample holding unit and the electrically conductive unit are integrally formed in a state where a part of the electrically conductive unit is buried in the biological sample holding unit.

In the electrical measurement of a biological sample, electrical continuity with a measuring circuit is made by electrical contacts being, from the electrical measuring device side, brought into contact with electrodes provided in a container or the like storing the biological sample. For a specific configuration of the electrical contact unit, for example, a component formed of a movable metal part and a fixed metal part or the like connected by a spring or the like is used as the electrical contact unit.

CITATION LIST

Patent Literature

PTL 1: JP 2009-042141A
PTL 2: JP 2010-181400A
PTL 3: JP 2014-115256A

SUMMARY

Technical Problem

When measuring the electrical characteristics of a biological sample, there is a problem that an electrical contact unit on the device side, a measuring circuit on the device side, etc. are damaged or contaminated by the inflow of a biological sample, a reagent, etc. into the device side from a container storing the biological sample or from the outside. Risk reduction is possible by figuring out an appropriate design of the structure of the container etc. in order to solve the problem, but substantial avoidance is difficult.

There is also a method in which the electrical contact unit on the device side is designed to be exchangeable and is exchanged at the time of damage or contamination. However, most of the parts used for the electrical contact unit are usually very small, and the exchange takes great time and effort.

Furthermore, when the biological sample is a liquid, the biological sample may enter the device via an electrical contact unit due to capillary action etc., and may break a substrate or a measuring circuit in the device.

In view of these, it is desirable to provide a technology capable of preventing a biological sample or a reagent from flowing into the device side.

Solution to Problem

Accordingly, some embodiments relate to a contact structure body that includes a separator and a contact probe. The separator physically separates a sample holder from a measuring circuit. The contact probe electrically connects an electrode of the sample holder to the measuring circuit.

In some embodiments, the contact probe include three different portions. A first portion of the contact probe disposed within the separator. A second portion of the contact probe disposed outside the separator and configured to be placed in physical contact with the electrode of the sample holder. A third portion of the contact probe is configured to be placed in physical contact with the measuring circuit.

Some embodiments relate to a system for determining a characteristic of a sample. The system includes a sample holder, a measuring circuit and a contact structure body. The sample holder hold the sample and includes an electrode. The measuring circuit measures at least one property of the sample. The contact structure body is attachable to and detachable from the sample holder and includes a separator and a contact probe. The separator physically separates the sample holder from the measuring circuit. The contact probe electrically connects the electrode of the sample holder to the measuring circuit.

Advantageous Effects of Invention

According to an embodiment of the present technology, it becomes possible to prevent a biological sample or a reagent prom flowing into the device side, and can consequently improve measurement precision.

BRIEF DESCRIPTION OF DRAWINGS

FIG. 1A is a schematic cross-sectional view schematically showing a first embodiment of a contact structure body 1 according to the present technology.

FIG. 1B is a schematic cross-sectional view schematically showing a state where the first embodiment of the contact structure body 1 according to the present technology is installed in an electrical measuring device for biological samples 10.

FIG. 2A is a schematic cross-sectional view schematically showing a second embodiment of a contact structure body 1 according to the present technology.

FIG. 2B is a schematic cross-sectional view schematically showing a state where the second embodiment of the contact structure body 1 according to the present technology is installed in an electrical measuring device for biological samples 10.

FIG. 3A is a schematic cross-sectional view schematically showing a third embodiment of a contact structure body 1 according to the present technology.

FIG. 3B is a schematic cross-sectional view schematically showing a state where the third embodiment of the contact structure body 1 according to the present technology is installed in an electrical measuring device for biological samples 10.

FIG. 4A is a schematic cross-sectional view schematically showing a fourth embodiment of a contact structure body 1 according to the present technology, FIG. 4B is a schematic cross-sectional view schematically showing a state where the fourth embodiment of the contact structure body 1 according to the present technology is installed in an electrical measuring device for biological samples 10.

FIG. 5 is a schematic cross-sectional view schematically showing the way of installing a fifth embodiment of the contact structure body 1 according to the present technology into the electrical measuring device for biological samples 10.

FIG. 6 is a schematic cross-sectional view schematically showing the way of installing a sixth embodiment of the contact structure body 1 according to the present technology into the electrical measuring device for biological samples 10.

FIG. 7 is a schematic cross-sectional view schematically showing a first embodiment of the electrical measuring device for biological samples 10 according to the present technology.

FIG. 8 is a schematic cross-sectional view schematically showing a second embodiment of the electrical measuring device for biological samples 10 according to the present technology and a container C inserted into a biological sample holding unit 101.

DESCRIPTION OF EMBODIMENTS

Hereinbelow, preferred embodiments for carrying out the present technology are described with reference to the drawings. The embodiments described below are examples of the typical embodiments of the present technology, and the scope of the present technology is not construed as being limited by the embodiments. The description is given in the following order:

1. Contact structure body 1
    (1) Contact probe 11
    (2) Separation unit 12
    (3) Substrate 13
    (4) Biological sample S
    2. Electrical measuring device for biological samples 10
    (1) Biological sample holding unit 101
    (2) Applying unit
    (3) Measuring unit
    (4) Analyzing unit
    (5) Memory unit
    (6) Display unit
    (7) User interface
    1. Contact structure body 1

FIG. 1A is a schematic cross-sectional view schematically showing a first embodiment of a contact structure body 1 according to the present technology, and FIG. 1B is a schematic cross-sectional view schematically showing a state where the contact structure body 1 according to an embodiment of the present technology is installed in an electrical measuring device for biological samples 10. FIG. 1B shows only a part of the electrical measuring device for biological samples 10.

The contact structure body 1 according to an embodiment of the present technology is a structure body used for the contact between electrodes E and a measuring circuit L in a device that electrically measures a biological sample (hereinafter, occasionally referred to as an "electrical measuring device for biological samples 10" or a "device 10"). The contact structure body 1 according to an embodiment of the present technology includes, in terms of broad categories, at least a contact probe 11 and a separation unit 12. The contact structure body 1 may include, as necessary, a substrate 13 etc. Each component will now be described in detail.

(1) Contact Probe 11

The contact probe 11 is provided to connect the electrode E used for measurement and the measuring circuit L when the contact structure body 1 according to an embodiment of the present technology is installed in the electrical measuring device for biological samples 10.

The contact probe 11 is made of an electrically conductive material. In the contact structure body 1 according to an embodiment of the present technology, the type of the electrically conductive material used for the contact probe 11 is not particularly limited, and one or more types of material usable for the electrical connection between the electrode E used for measurement and the measuring circuit L may be freely selected to use. For example, titanium, aluminum, stainless steel, platinum, gold, copper, graphite, and the like are given.

Specific structures of the contact probe 11 are not particularly limited, to the extent that the electrode E and the measuring circuit L can be electrically connected, and may be freely designed. For example, like the contact structure body 1 according to the first embodiment of FIG. 1, a connection unit for connection to the electrode E and/or a connection unit for connection to the measuring circuit L may be designed in the form of a spring structure 11s; thereby, a bad connection etc. can be prevented. By way of example and not limitation, the spring structure may be a leaf spring.

In the contact structure body 1 according to an embodiment of the present technology, the number of contact probes 11 is not particularly limited, to the extent that one or more contact probes 11 are provided for the electrode E used for measurement, and may be freely designed. For example, although not shown in the drawings, a plurality of contact probes 11 may be freely provided for each one of the electrodes E used for measurement. By providing a plurality of contact probes 11 for each one of the electrodes E used for measurement, contact redundancy is improved, and the rate of bad contact caused by dust, abrasion, etc. can be reduced, for example.

(2) Separation Unit 12

The separation unit 12 is provided to separate the measuring circuit L and a biological sample holding unit 101 for holding a biological sample S when the contact structure body 1 according to an embodiment of the present technology is installed in the electrical measuring device for biological samples 10. The separation unit 12 includes a leak liquid storage unit 121 that stores leak liquid. As the leak liquid, for example, a biological sample S or a reagent R leaked from the biological sample holding unit 101, a biological sample S or a reagent R that has accidentally flowed in from the outside during injection into the biological sample holding unit 101 or the like, a cleaning liquid for cleaning the biological sample holding unit 101, etc. are given. The leak from the biological sample holding unit 101 may be generated from a bonding part of the biological sample holding unit 101 and the electrode E, for example.

The configuration of the leak liquid storage unit 121 is not particularly limited, to the extent that leak liquid can be stored, and may be freely designed. For example, the leak liquid storage unit 121 may be formed in a cup-like configuration like the contact structure body 1 according to the first embodiment of FIG. 1, or may be designed in a configuration spreading planarly on the upper side or the lower side of the substrate 13 like the contact structure body 1 according to a second embodiment of FIG. 2 or a third embodiment of FIG. 3.

Also the storage capacity of the leak liquid storage unit 121 is not particularly limited, and may be freely designed in accordance with the amount of the biological sample S of the measuring object or the reagent R, the structure of the device, etc. For example, when the storage capacity of the leak liquid storage unit 121 is designed to be larger than the storage capacity of the biological sample holding unit 101 used for measurement, the entry of leak liquid into the device can be prevented reliably.

The separation unit 12 may be made of any non-electrically conductive material, and the type of the non-electrically conductive material used is not particularly limited and one or more types of known non-electrically conductive material may be freely selected for use. For example, a resin or the like may be used.

(3) Substrate 13

FIG. 4A is a schematic cross-sectional view schematically showing a fourth embodiment of a contact structure body 1 according to the present technology, and FIG. 4B is a schematic cross-sectional view schematically showing a state where the contact structure body 1 according to an embodiment of the present technology is installed in an electrical measuring device for biological samples 10. FIG. 4B shows only a part of the electrical measuring device for biological samples 10.

The contact structure body 1 according to an embodiment of the present technology may include the substrate 13 provided with the measuring circuit L. The substrate 13 is not essential for the contact structure body 1 according to an embodiment of the present technology, and may be included in the electrical measuring device for biological samples 10 beforehand as shown in FIGS. 1 to 3; but when the contact structure body 1 includes the substrate 13, the distance between the measurement reference point and the biological sample S can be shortened and measurement errors etc. can be reduced. Furthermore, when the contact structure body 1 includes the substrate 13, the exchange can be made wholly together with the substrate 13 quickly and easily, even in the unlikely event of leakage trouble of the biological sample S or the reagent R. Consequently, device performance can be maintained while the number of support steps can be reduced due to the ease of exchange and the total maintenance costs can be reduced, with limited unit costs of parts.

The material that forms the substrate 13 is not particularly limited, and one or more types of known material used for a substrate provided with an interconnection circuit may be freely selected for use. Also the configuration of the interconnection circuit L may be freely designed in accordance with the objective of measurement.

FIG. 5 is a schematic cross-sectional view schematically showing the way of installing a fifth embodiment of the contact structure body 1 according to the present technology into the electrical measuring device for biological samples 10. The contact structure body 1 according to the fifth embodiment is an example that enables attachment and detachment to/from the electrical measuring device for biological samples 10. By enabling attachment and detachment, the contact structure body 1 can be easily exchanged wholly, for example when leak liquid has collected in the leak liquid storage unit 121 of the separation unit 12, when dust or damage has occurred on the contact probe 11, or in other cases.

In the case where the contact structure body 1 according to an embodiment of the present technology is configured to be attachable and detachable, its structure is not particularly limited. For example, by providing a slide mechanism such as a rail, insertion and alignment to the device 10 can be made easier. Furthermore, by providing an alignment pin or the like, the contact structure body 1 and the device 10 can be fixed while alignment is made.

Also the direction when the contact structure body 1 according to an embodiment of the present technology is attached and detached is not particularly limited. Attachment and detachment may be performed from the lateral side of the device 10 like, for example, the fifth embodiment shown in FIG. 5, or may be performed from the lower side of the device 10 like, for example, a sixth embodiment shown in FIG. 6. This may be achieved, for example, by including tabs on the side of the contact structure body that fit into corresponding recessed portions of the device when attached, as illustrated in FIG. 6.

(4) Biological Sample S

The biological sample S that can be the measuring object in an embodiment of the present technology is not particularly limited and may be freely selected. For measurement using the contact structure body 1 according to an embodiment of the present technology, in particular a biological sample S in a liquid form can be suitably used. As the biological sample S in a liquid form, a blood sample is given, for example. More specifically, a biological sample containing a blood component such as whole blood, blood plasma, or a diluted solution and/or a drug-added substance thereof, etc. may be given.

2. Electrical Measuring Device for Biological Samples 10

FIG. 7 is a schematic cross-sectional view schematically showing a first embodiment of the electrical measuring device for biological samples 10 according to the present technology. The electrical measuring device for biological samples 10 according to an embodiment of the present technology includes, in terms of broad categories, at least the biological sample holding unit 101, an applying unit, a measuring unit, and the contact structure body 1. The electrical measuring device for biological samples 10 may include, as necessary, an analyzing unit, a memory unit, a display unit, a user interface, etc. Each component will now be described in detail. The contact structure body 1 is as described above, and a description is omitted herein.

(1) Biological Sample Holding Unit 101

The biological sample holding unit 101 is provided to store the biological sample S. The electrical characteristics of the biological sample S are measured in a state where the biological sample S is held by the biological sample holding unit 101.

The configuration of the biological sample holding unit 101 is not particularly limited, to the extent that the biological sample S can be stored and held, and may be freely designed. For example, like the first embodiment of FIG. 7, a space where the biological sample S can be held may be provided in the device 10, and the biological sample S may be directly stored in the space. Furthermore, for example, an attachable and detachable disposable container C may be used by, for example, designing a configuration in which the container C that stores the biological sample S can be held like a second embodiment of FIG. 8.

By using an attachable and detachable disposable container as the container C, the time and effort of cleaning of the container C etc. can be omitted, and the efficiency of measurement can be improved. Furthermore, the occurrence of measurement errors etc. due to other biological samples S or reagents R remaining in the container C can be prevented, and measurement precision can be improved.

In the case where the container C is used, configurations of the container C are not particularly limited, and may be freely designed in accordance with the condition, measuring method, etc. of the biological sample S to the extent that the biological sample S of the measuring object can be held, including a circular cylindrical body, a polygonal cylindrical body with a polygonal cross section (triangle, quadrangle, or polygon with more angles), a conical body, a polygonal pyramid-like body with a polygonal cross section (triangle, quadrangle, or polygon with more angles), or a configuration in which one or more of these are combined.

Also the material that forms the container C is not particularly limited, and may be freely selected to the extent that there is no influence on the condition, measurement objective, etc. of the biological sample S of the measuring object. In the present technology, in particular, the container C is preferably formed using a resin from the viewpoint of the ease of processing and molding etc. In the present technology, also the type of usable resin is not particularly limited, and one or more types of resin usable for the holding of the biological sample S may be freely selected for use. For example, a hydrophobic and insulating polymer such as polypropylene, poly(methyl methacrylate), polystyrene, an acrylic, a polysulfone, and polytetrafluoroethylene, a copolymer and a blend polymer thereof, and the like are given. In an embodiment of the present technology, the container S is preferably formed of, among the above materials, particularly one or more types of resin selected from polypropylene, polystyrene, an acrylic, and a polysulfone. These resins have the property of being low coagulation-active against blood, and can therefore be suitably used for the measurement of the biological sample S containing blood, for example.

It is also possible to enclose the reagent R in the container C beforehand. That is, the transfer, preservation, etc. of the container C can be made in a state where the reagent R is enclosed beforehand. By enclosing the reagent R beforehand, simplification during measurement can be achieved. In addition, the reagent R can be prevented from flowing into the device 10 during the injection of the reagent R. In addition, an effective amount of the reagent for the biological sample S can be kept. In this case, the type of the reagent R is not particularly limited and may be freely selected. For example, reagents in a gas form, a solid form, a liquid form, etc. are given. As the reagent in a liquid form, specifically, an anticoagulant, a coagulation initiator, etc. are given when a biological sample S containing a blood component is used as the measuring object or in other cases.

The biological sample holding unit 101 is preferably in a configuration capable of being sealed in the state of holding the biological sample S. However, the biological sample holding unit 101 may not be in an airtight configuration to the extent that it is capable of being stationary through the time expected to measure the electrical characteristics of the biological sample S and there is no influence on measurement.

The biological sample holding unit 101 may include the electrode E. However, the electrode E is not essential for the electrical measuring device for biological samples 10. It is also possible, although not shown in the drawings, to insert the electrode E from the outside into the biological sample S in the biological sample holding unit 101 at the time of measurement and measure the electrical characteristics of the biological sample S. Furthermore, as shown in FIG. 8, when a disposable container C is used, the container C may include the electrode E.

The type of the material used for the electrode E is not particularly limited, to the extent that it is a material with electrical conductivity, and one or more types of material usable for the electrical measurement of the biological sample S may be freely selected for use. For example, titanium, aluminum, stainless steel, platinum, gold, copper, graphite, and the like are given. In the present technology, the electrode E is preferably formed of, among the above materials, particularly an electrically conductive material containing titanium. Titanium has the property of being low coagulation-active against blood, and can therefore be suitably used for the measurement of a biological sample S containing blood, for example.

In an embodiment of the present technology, the number of electrodes E may be freely designed in accordance with the method of the electrical measurement of the objective etc. For example, a pair or more of electrodes E may be used when the dielectric constant or the impedance of the biological sample S is measured.

(2) Applying Unit

The applying unit is provided to apply a voltage to the electrodes E used for measurement. The applying unit applies a voltage to the electrodes E from, as the starting time point, the time point at which an order to start measurement is received or the time point at which the power supply for the electrical measuring device for biological samples 10 is set to ON. More specifically, the applying unit applies an AC voltage with a prescribed frequency to the electrodes E at set measuring intervals. The voltage that the applying unit applies may be a DC voltage in accordance with the electrical characteristics to be measured.

(3) Measuring Unit

The measuring unit is provided to measure the electrical characteristics of the biological sample S held by the biological sample holding unit 101. Specifically, electrical characteristics such as complex dielectric constant (hereinafter, occasionally simply referred to as "dielectric constant") or its frequency dispersion are measured from, as the starting time point, the time point at which an order to start measurement is received or the time point at which the power supply for the electrical measuring device for biological samples 10 is set to ON. More specifically, for example, when the dielectric constant is measured, the measuring unit measures the current or the impedance between the electrodes E used for measurement at prescribed intervals, and derives the dielectric constant from the measured value. For the derivation of the dielectric constant, a known function or mathematical relation expressing the relationship between the current or the impedance and the dielectric constant may be used.

As the electrical characteristics measurable in the measuring unit, for example, dielectric constant, impedance, admittance, capacitance, conductance, electrical conductivity, phase angle, etc. may be given. These electrical characteristics can be transformed to each other by the mathematical formulae shown in Table 1 below. Therefore, for example, when a blood sample is used as the biological sample S, the estimation results of the hematocrit value and/or the hemoglobin amount when estimated using the results of the dielectric constant measurement of the blood sample are the same as the estimation results when estimated using the results of the impedance measurement of the same blood sample. Most of these electrical quantities and property values can be described using complex numbers, and the transformation formula can thereby be simplified.

TABLE 1

Principal electrical quantities and property values mutually transformable

| Electrical quantity and property value | Symbol | When expressed using complex number |
|---|---|---|
| Voltage | V | $V^* = \|V\| \exp j(\omega t + \phi)$ |
| Current | I | $I^* = \|I\| \exp j(\omega t + \phi)$ |
| Impedance | Z | $Z^* = R + jX$ (R: resistance, X: reactance) |
| Admittance | Y | $Y^* = G + jB$ (g: conductance, B: susceptance) |
| Capacitance | C | $C^* = C - jG/\omega$ |
| Conductance | G | $G^* = G + j\omega C$ |
| Loss tangent (dielectric loss tangent) | D or tan δ | |
| Loss angle | δ | |
| Phase angle | θ | |
| Q factor | Q | |
| Dielectric constant | ε | $\varepsilon^* = \varepsilon - j\kappa/\omega\varepsilon_0$ |
| Electrical conductivity | κ | $\kappa^* = \kappa + j\omega\varepsilon_0\varepsilon$ |

Mathematical formula relating each electrical and property value $Z^* = V^*/I^*$ $\theta = \Phi - \varphi$ $Y^* = 1/Z^*$ $C = B/\omega$ $D = \tan \delta = G/\omega C = 1/Q$ $\varepsilon^* = C^*/C_0$ $\kappa^* = j\omega\varepsilon_0\varepsilon^*$ ω: angular frequency
$\varepsilon_0$: dielectric constant of vacuum (constant)
$C_o$: constant depending on measuring device etc.
Value marked with *: complex number In the measuring unit, the frequency band in which electrical measurement is performed may be appropriately selected in accordance with the condition, measurement objective, etc. of the biological sample S to be measured. For example, when the biological sample S to be measured is blood and the electrical characteristic is impedance, a change is seen in the frequency bands shown in Table 2 below in accordance with the condition change of the blood.

TABLE 2

| | Impedance | |
|---|---|---|
| Condition change of blood | Frequency at which change is seen | Frequency at which change is more significant |
| Coagulation of blood (blood coagulation) | 1 kHz to 50 MHz | 3 MHz to 15 MHz |
| Fibrin formation | 1 kHz to 50 MHz | 3 MHz to 15 MHz |
| Fibrin clot formation | 1 kHz to 50 MHz | 3 MHz to 15 MHz |
| Blood clot formation | 1 kHz to 50 MHz | 3 MHz to 15 MHz |
| Rouleaux formation of red blood cells | 500 kHz to 25 MHz | 2 MHz to 10 MHz |
| Aggregation of blood | 1 kHz to 50 MHz | 500 kHz to 5 MHz |
| Sedimentation of red blood cells (erythrocyte sedimentation) | 1 kHz to 50 MHz | 100 kHz to 40 MHz |
| Blood dot retraction (retraction) | 1 kHz to 50 MHz | 10 kHz to 100 kHz |
| Hemolysis | 1 kHz to 50 MHz | 3 MHz to 15 MHz |
| Fibrinolysis | 1 kHz to 50 MHz | 3 MHz to 15 MHz |

For example, in the case where the objective is to predict or detect the coagulation of blood (blood coagulation), it is preferable to measure the impedance at frequencies of 1 kHz to 50 MHz, and it is more preferable to measure the impedance at frequencies of 3 MHz to 15 MHz. By setting a parameter in accordance with the condition or measurement objective of the biological sample S beforehand in this way, a preferable frequency band like those shown in Table 2 above can be automatically selected.

(4) Analyzing Unit

The electrical measuring device for biological samples 10 according to an embodiment of the present technology may include the analyzing unit that receives the electrical characteristic data of the biological sample S derived from the measuring unit and determines the properties of the biological sample S, or performs other things. In the electrical measuring device for biological samples 10 according to an embodiment of the present technology, the analyzing unit is not essential; it is also possible to perform analysis from the electrical characteristic data measured in the measuring unit using an external computer or the like, for example. Specifically, the electrical characteristic data of the biological sample S derived from the measuring unit are given to the analyzing unit at measuring intervals, and the analyzing unit receives the electrical characteristic data given from the measuring unit and starts the property determination etc. of the biological sample S. The analyzing unit notifies the results of the property determination etc. and/or the dielectric constant data of the biological sample S. The notification may be made by making a graph and displaying it on a display unit described later, such as a monitor, or printing on a prescribed medium, for example.

(5) Memory Unit

The electrical measuring device for biological samples 10 according to an embodiment of the present technology may include the memory unit that stores the measurement results measured in the measuring unit, the analysis results analyzed in the analyzing unit, etc. In the electrical measuring device for biological samples 10 according to an embodiment of the present technology, the memory unit is not essential, and the results may be stored by connecting an external memory device.

In the electrical measuring device for biological samples 10 according to an embodiment of the present technology, the memory unit may be provided separately for each unit, or may be designed so that various results obtained in the units are stored in one memory unit.

(6) Display Unit

The electrical measuring device for biological samples 10 according to an embodiment of the present technology may include the display unit that displays the measurement results measured in the measuring unit, the analysis results analyzed in the analyzing unit, etc. In the electrical measuring device for biological samples 10 according to an embodiment of the present technology, the display unit is not essential, and the results may be displayed by connecting a display device such as an external monitor.

In the electrical measuring device for biological samples 10 according to an embodiment of the present technology, the display unit may be provided separately for each unit, or may be designed so that various results obtained in the units may be collectively displayed on one display unit.

(7) User Interface

The electrical measuring device for biological samples 10 according to an embodiment of the present technology may include the user interface for a user's operation. In the electrical measuring device for biological samples 10 according to an embodiment of the present technology, the user interface is not essential, and the device 10 may be designed to be used in conjunction with an external computer to enable operation from the outside.

In the case where the analyzing unit, the memory unit, the display unit, the user interface, etc. described above are provided outside the device 10, these may be connected to each other via a network.

It should be understood by those skilled in the art that various modifications, combinations, sub-combinations and alterations may occur depending on design requirements and other factors insofar as they are within the scope of the appended claims or the equivalents thereof.

For example, aspects of some configurations of various embodiments include:

(1) A contact structure body comprising:

a separator configured to physically separate a sample holder from a measuring circuit;

a contact probe configured to electrically connect an electrode of the sample holder to the measuring circuit, the contact probe comprising:

a first portion of the contact probe disposed within the separator;

a second portion of the contact probe disposed outside the separator and configured to be placed in physical contact with the electrode of the sample holder; and a third portion of the contact probe configured to be placed in physical contact with the measuring circuit.

(2) The contact structure body of claim 1, wherein the second portion of the contact probe comprises a first spring structure and the third portion of the contact probe comprises a second spring structure.

(3) The contact structure body of configuration 1, wherein the separator comprises a liquid storage unit configured to store liquid leaked from the sample holder.

(4) The contact structure body of configuration 3, wherein:

the contact probe is a first contact probe;

the contact structure body comprises a second contact probe; and the liquid storage unit is disposed between the first contact probe and the second contact probe.

(5) The contact structure body of configuration 3, wherein:

the liquid storage unit is disposed between the measuring circuit and the sample holder.

(6) The contact structure body of configuration 3, wherein:

the measuring circuit is disposed between the liquid storage unit and the sample holder.

(7) The contact structure body of configuration 1, wherein the contact structure body comprises the measuring circuit.

(8) The contact structure body of configuration 1, further configured to be attachable to and detachable from a measuring device.

(9) The contact structure body of configuration 8, further configured to be attachable to and detachable from a lateral side of the measuring device.

(10) The contact structure body of configuration 8, further configured to be attachable to and detachable from a bottom side of the measuring device

(11) The contact structure body of configuration 1, wherein the measuring circuit is configured to measure an electrical property of a sample disposed in the sample holder.

(12) The contact structure body of configuration 11, wherein the electrical property is at least one of a dielectric constant and a frequency dispersion.

(13) The contact structure body of configuration 1, wherein the measuring circuit includes an analyzing circuit configured to determine a characteristic of blood coagulation.

(14) The contact structure body of configuration 1, wherein the third portion of the contact probe is disposed outside the separator.

(15) A system for determining a characteristic of a sample, the system comprising:

a sample holder configured to hold the sample, the sample holder comprising an electrode;

a measuring circuit configured to measure at least one property of the sample;

a contact structure body configured to be attached to and detached from the sample holder, the contact structure body comprising:

a separator configured to physically separate the sample holder from the measuring circuit; and a contact probe configured to electrically connect the electrode of the sample holder to the measuring circuit.

(16) The system of configuration 15, wherein the sample holder is configured to receive a disposable sample container.

(17) The system of configuration 16, wherein the disposable sample container includes an electrode configured to contact the electrode of the sample holder.

(18) The system of configuration 15, further comprising a voltage supplier configured to apply a voltage to the electrode of the sample holder.

(19) The system of configuration 15, further comprising an analyzer configured to analyze the at least one property measured by the measuring circuit and determine the at least one characteristic of the sample.

(20) The system of configuration 15, wherein the system is a coagulometer.

(21) The system of configuration 15, wherein the at least one property is at least one of a dielectric constant and a frequency dispersion.

REFERENCE SIGNS LIST 1 contact structure body
11 contact probe
11s spring structure
12 separation unit
121 leak liquid storage unit
13 substrate
S biological sample
10 electrical measuring device for biological samples
101 biological sample holding unit
E electrode
L measuring circuit

The invention claimed is:

1. A contact structure body comprising:
a separator configured to physically separate a liquid leaked from a sample holder from a measuring circuit;
a contact probe configured to electrically connect an electrode of the sample holder to the measuring circuit, the contact probe comprising:
a first portion of the contact probe disposed within the separator;
a second portion of the contact probe disposed outside the separator and configured to be placed in physical contact with the electrode of the sample holder; and
a third portion of the contact probe configured to be placed in physical contact with the measuring circuit,
wherein the separator is further configured to physically separate the liquid leaked from the contact probe.

2. The contact structure body of claim 1, wherein the second portion of the contact probe comprises a first spring structure and the third portion of the contact probe comprises a second spring structure.

3. The contact structure body of claim 1, wherein the separator comprises a liquid storage unit configured to store liquid leaked from the sample holder.

4. The contact structure body of claim 3, wherein:
the contact probe is a first contact probe;
the contact structure body comprises a second contact probe; and
the liquid storage unit is disposed between the first contact probe and the second contact probe.

5. The contact structure body of claim 3, wherein:
the liquid storage unit is disposed between the measuring circuit and the sample holder.

6. The contact structure body of claim 3, wherein:
the measuring circuit is disposed between the liquid storage unit and the sample holder.

7. The contact structure body of claim 1, wherein the contact structure body comprises the measuring circuit.

8. The contact structure body of claim 1, further configured to be attachable to and detachable from a measuring device.

9. The contact structure body of claim 8, further configured to be attachable to and detachable from a lateral side of the measuring device.

10. The contact structure body of claim 8, further configured to be attachable to and detachable from a bottom side of the measuring device.

11. The contact structure body of claim 1, wherein the measuring circuit is configured to measure an electrical property of a sample disposed in the sample holder.

12. The contact structure body of claim 11, wherein the electrical property is at least one of a dielectric constant and a frequency dispersion.

13. The contact structure body of claim 1, wherein the measuring circuit includes an analyzing circuit configured to determine a characteristic of blood coagulation.

14. The contact structure body of claim 1, wherein the third portion of the contact probe is disposed outside the separator.

15. A system for determining a characteristic of a sample, the system comprising:
a sample holder configured to hold the sample, the sample holder comprising an electrode;
a measuring circuit configured to measure at least one property of the sample;
a contact structure body configured to be attached to and detached from the sample holder, the contact structure body comprising:
a separator configured to physically separate the sample holder and/or liquid leaked from the sample holder from the measuring circuit; and
a contact probe configured to electrically connect the electrode of the sample holder to the measuring circuit,
wherein the separator is further configured to physically separate the liquid leaked from the contact probe.

16. The system of claim 15, wherein the sample holder is configured to receive a disposable sample container.

17. The system of claim 16, wherein the disposable sample container includes an electrode configured to contact the electrode of the sample holder.

18. The system of claim 15, further comprising a voltage supplier configured to apply a voltage to the electrode of the sample holder.

19. The system of claim 15, further comprising an analyzer configured to analyze the at least one property measured by the measuring circuit and determine the at least one characteristic of the sample.

20. The system of claim 15, wherein the system is a coagulometer.

21. The system of claim 15, wherein the at least one property is at least one of a dielectric constant and a frequency dispersion.

* * * * *